United States Patent [19]

Matterson

[11] Patent Number: 4,530,113
[45] Date of Patent: Jul. 23, 1985

[54] VASCULAR GRAFTS WITH CROSS-WEAVE PATTERNS

[75] Inventor: Samuel A. Matterson, Coalville, England

[73] Assignee: Intervascular, Inc., Freeport, Tex.

[21] Appl. No.: 496,454

[22] Filed: May 20, 1983

[51] Int. Cl.³ .......................... A61F 1/00; D03D 3/02
[52] U.S. Cl. .................................. 623/1; 128/334 R; 139/387 R; 139/388; 623/12
[58] Field of Search ................................ 3/1.4, 1 A, 1; 128/334 R; 139/387 R, 388

[56] References Cited

U.S. PATENT DOCUMENTS

| 955,541 | 4/1910 | Petersen | 139/387 R |
| 1,139,467 | 5/1915 | Cole | 139/388 |
| 3,316,557 | 5/1967 | Liebig | 128/334 R |
| 4,193,137 | 3/1980 | Heck | 3/1 A |

Primary Examiner—Richard J. Apley
Assistant Examiner—Greg Beaucage
Attorney, Agent, or Firm—Fitch, Even, Tabin & Flannery

[57] ABSTRACT

Graft prostheses are woven with cross-weave patterns to prevent unravelling and to increase suture hold strength. A vascular graft according to the invention is woven as a continuous tube by shuttling a continuous weft thread through a double-layer array of warp threads. As the weft thread is shuttled through the warp pattern, groups of warp threads are retained in parallel relationship to each other while interspersed pairs of warp threads are crossed over each other. This results in graft having normal weave patterns circumferentially alternating with cross-weave patterns.

21 Claims, 6 Drawing Figures

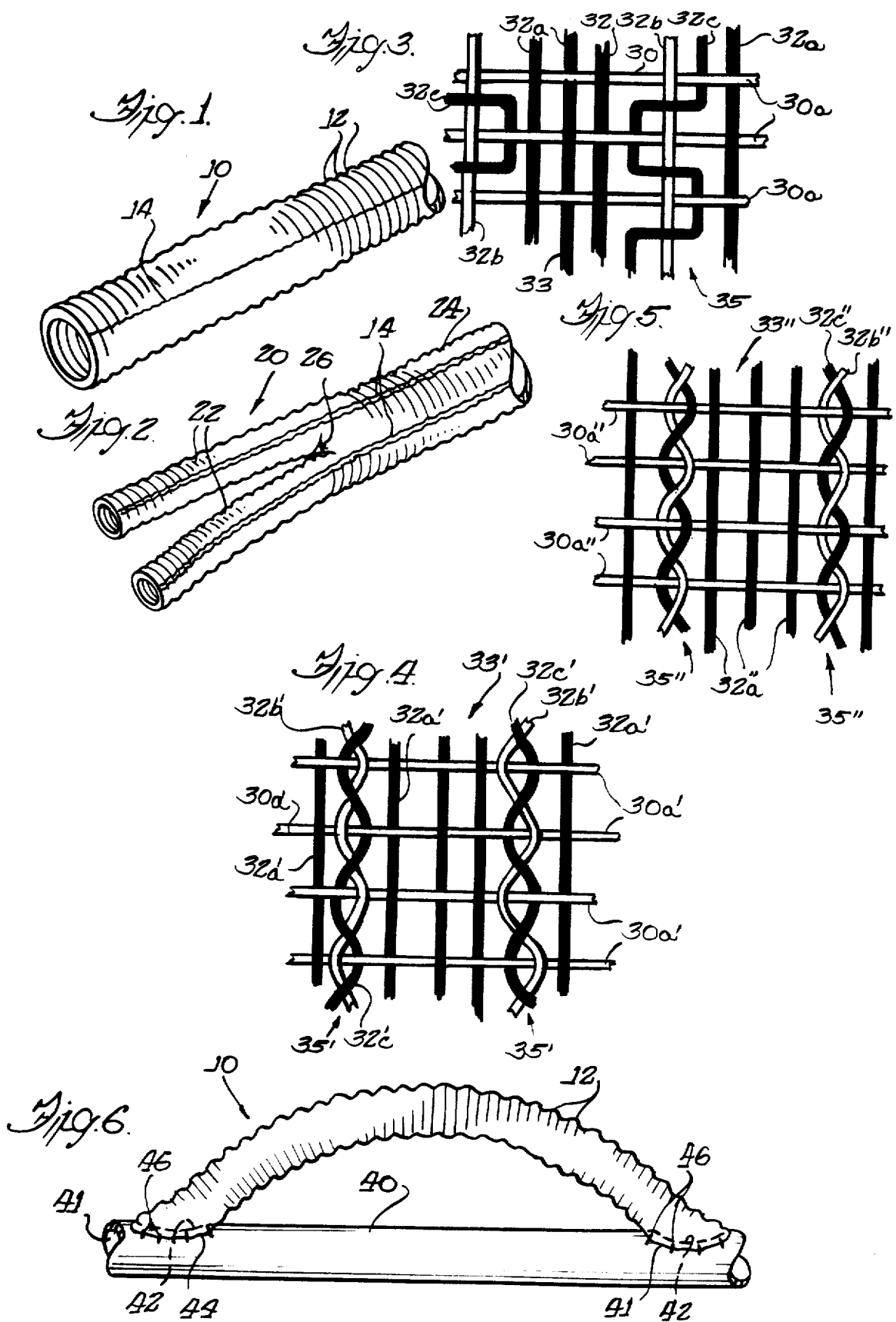

VASCULAR GRAFTS WITH CROSS-WEAVE PATTERNS

The present invention relates to fabric grafts and more particularly to woven vascular grafts.

BACKGROUND OF THE INVENTION

Vascular graft prostheses are widely used in a variety of surgical procedures. Grafts may be used to replace sections of natural blood vessels which have been removed either through accident or through surgery. Grafts might also be used to provide an alternative route for blood, e.g., to bypass an especially occluded portion of an arteriosclerotic vessel, or might be used to form a new blood pathway in vascular reconstruction procedures.

The most common type of vascular prosthesis is a fabric graft, which may be either woven, knitted or velour. The earliest grafts were generally woven; however, later it became accepted that knitted grafts had advantages over woven grafts for many applications. Particular advantages which have been ascribed to knitted grafts include their high porosity, softness and flexibility and the potentially high velour index of their surfaces, which was felt to promote healing through endotheliazation, i.e., ingrowth of tissue. It is found, however, that endotheliazation occurs to a considerably lesser degree in vascular prostheses implanted in humans than was previously predicted, and thus, certain of the advantages that were previously ascribed to knitted prostheses have not been realized. In fact, it has been found that the high velour surfaces of knitted grafts may simply act to collect dead tissue, particularly on their interior surface.

Woven grafts have certain recognized advantages over knitted grafts. They can be made with a porosity which is lower than the porosity available in knitted prostheses and can be constructed with greater fabric uniformity, e.g., their porosity is more uniform. In the weaving process, the weft thread is mechanically compacted and pushed against the adjacent weft thread, leaving either substantially no pores or very small pores. In certain instances, such as where the patient has been administered anticoagulants or for certain types of vascular repair, a prosthesis through which blood does not seep at all is required, and for such applications the graft should have a very low porosity which is only available in a woven graft.

Where pores do exist in either a knitted or a woven fabric, which would otherwise allow blood to seep through, the pores are generally closed by preclotting. The patient's own peripheral blood is drawn, the graft is spun in the patient's blood to uniformly soak the graft and the blood-drenched graft is exposed to air for a short period of time which is sufficient for fibrin to build up within the pores and close the pores. Even for applications where preclotting may be used, a porosity lower than that which is generally attainable in a knitted graft is desirable to insure fluid integrity of the graft, and in this respect, woven grafts have an important advantage over knitted grafts. Woven grafts are therefore returning to favor for use in applications where knitted grafts had recently been preferred.

Typically, a graft is woven in a tubular configuration in which the weft or pick is actually a single long thread shuttled helically through a two-layer array of warp threads, as described in U.S. Pat. No. 3,316,557, forming a flat tubular configuration. The tubular configuration is then opened to a cylindrical configuration, set and crimped. One problem that is still presented by woven grafts is their tendency under certain conditions to unravel. A vascular graft is usually supplied with excess length and is subsequently cut by the surgeon. Whereas a knitted graft can be knitted in a manner that substantially eliminates unravelling after it is cut, a woven graft is typically left with at least one end that is partially frayed due to cutting. A frayed fabric end of a woven graft may promote progressive unwinding of the helically wound weft thread, resulting in eventual weakening of the graft. This fraying problem has tended to limit the use of woven vascular grafts even when their low porosity and other advantages, such as higher mechanical strength, would otherwise indicate their use. It would be advantageous to have a woven graft which is not subject to unravelling.

SUMMARY OF THE INVENTION

Woven grafts are provided having a weave pattern that is at least in part a cross-weave pattern, such as gauze weave, a leno weave or a helical weave. Generally, a graft according to the invention includes a normal weave pattern circumferentially alternating with the cross-weave pattern. A vascular graft is woven as a large longitudinal tube (or in the case of smaller bifurcated graft as a longitudinal tube which splits into a pair of smaller longitudinal tubes) in which a longitudinal warp pattern is filled with a continuous, helically wound weft thread. The warp pattern includes pairs of threads that are crossed over each other repeatedly during the weaving process, preferably with a pass of the weft thread between each pair of successive warp thread cross-over points. The warp pattern preferably includes one or more parallel threads between successive pairs of cross-woven warp threads, the parallel threads being woven in a normal weave pattern, such a 1/1 weave. Because the weft is locked in the warp pattern by crossed warp threads, the weft thread is substantially restrained against unravelling and therefore has high suture hold. The woven graft has lower porosity than a comparable knitted graft.

BRIEF DESCRIPTION OF THE DRAWINGS

FIG. 1 is a perspective view of a woven tubular graft, embodying various features of the invention;

FIG. 2 is a perspective view of a bifurcated graft embodying various features of the invention;

FIG. 3 is a diagrammatic illustration of a cross-weave pattern particularly useful in either of the grafts of FIGS. 1 and 2;

FIG. 4 is a diagrammatic illustration of an alternative cross-weave pattern;

FIG. 5 is a diagrammatic illustration of another alternative cross-weave pattern; and FIG. 6 is a perspective view of a tubular graft woven according to the invention which is cut diagonally at its ends and being used as a shunt to form a bypass blood-flow pathway.

DETAILED DESCRIPTION OF THE PREFERRED EMBODIMENTS

Woven grafts or prostheses are provided which are highly resistant to unravelling. In accordance with the invention, fabric grafts are woven at least partially in what will be generally referred to herein as a cross-weave pattern in which certain warp threads are crossed with another by pulling them out of their normal straight and parallel course, first to one side and then to the other side, while weft thread is shuttled between the crossed warp threads. Cross-weaving for purposes of this invention includes leno weaving, gauze weaving, helical weaving and variations thereof. Certain preferred examples of suitable cross-weaves will be described herein, it being understood that countless variations of the basic patterns are known, and appropriate variations are considered equivalents for purposes of this invention. The weft, which is shuttled through the crossed warp threads, is "locked" between cross point of the warp threads and thereby substantially restrained against unravelling, even if a tubular graft structure is cut at an angle.

The weave for forming the prosthesis is generally not strictly a cross-weave pattern but preferably consists of normal weave patterns interspersed with cross-weave patterns. For purposes of this invention, a normal weave pattern will be a weave pattern in which parallel wrap threads are crossed with a substantially perpendicular weft or pick. For example, a typical warp thread pattern may alternate groups of three parallel warp threads with pairs of crossed warp threads.

The final product of the process appears on a macro level to be the same as woven or knitted grafts previously described. Illustrated in FIG. 1 is a tubular vascular graft 10 which might be used to replace a linear section of a blood vessel. A fabric tube is woven flat in a continuous process and then heat-set and crimped to form a cylindrical tube that has circumferential corrugations 12 that expand and contract in accordion or pleated fashion to provide a variable axial length. The tube 10 is cut into individual lengths, each length being somewhat longer than the anticipated need, and then packaged and sterilized. As is conventional, a longititudinal marking or markings 14 is provided, e.g., by the inclusion of one or more black warp threads in the weave pattern of the graft or by printing or dyeing.

Illustrated in FIG. 2 is a bifurcated graft 20 useful for replacing a branched portion of a blood vessel. With an appropriate loom, such as a narrow fabric shuttle loom, a pair of narrower diameter tubular portions 22 are woven continuous of one end of a larger diameter tubular portion 24, leaving an opening at the bifurcation. A crotch region 26 is formed by sewing closed the opening at the bifurcation in a conventional manner.

Illustrated in FIG. 3 is diagrammatic illustration a preferred weave pattern used in vascular grafts according to the invention. The weave pattern consists of a plurality of parallel weft segments of picks 30a woven through a pattern of warp threads which include three straight parallel warp threads 32a alternating with pairs of crossed warp threads 32b,c. This results in normal weave patterns 33 being circumferentially interspersed with narrow cross-weave patterns 35. In the vascular graft prosthesis 10, the warps or ends 32 run in the axial direction while the individual picks 30a are actually segments of a continuous, helically wound weft thread 30. The pick 30a is shuttled through the groups of parallel warp threads 32a in a 1/1 or plain pattern, and each pick passes through an opening between the cross points of the crossed warp threads.

The cross-weave portion 35 of the weave pattern illustrated in FIG. 3 is a simple gauze pattern in which one thread 32b of the pair of crossed threads, represented as a substantially straight thread, is held under higher tension and is referred to as a "regular" or "standard" thread, whereas the other crossed warp thread 32c, represented as a thread with right angle bends, is under less tension, follows a significantly longer path than the standard thread and is referred to as the "doup" thread. The gauze pattern 35 is woven on a loom which provides a separate beam for the standard threads and for doup threads, the separate beams permitting the tension on the two types of threads to differ and the doup threads to be played out to a longer length than the length of the standard threads. Weaving of a gauze pattern and other cross-weave patterns is described in greater detail in *Watson's Advance Textile Design* V. Crosicki (4th Edition) Butterworth & Co. (1977), the teachings of which are incorporated herein by reference.

In the simple gauze weave, each pick 30a passes to one side (below in the illustration) of the standard warp thread 32b and to the other side (above) of the doup thread 32c. The doup thread 32c crosses above each standard thread 32b between adjacent picks 30a. Through the cross-weave pattern, each pick 30a is "locked" within each passage it makes through an opening formed by a pair of crossed warp threads 30b,c, and this interlocking of the picks restrains the picks from axial displacement from each other and thereby substantially restrains the picks against unravelling from the cut ends of the woven prosthesis 10. As illustrated in FIG. 3, the relative position of the standard and the doup threads is preferably reversed in each successive cross-weave portion 35 circumferentially about the tube.

At the present time, the inventors regard the gauze weave 35 as the preferred cross-weave pattern because for the type of threads used in the tube-forming loom, the gauze pattern is relatively simple to weave, effectively prevents unravelling, and allows continuous control of porosity to establish particularly uniform porosity, which can be lower than that of other such weaves.

Illustrated in FIG. 4 is another embodiment of a weave pattern, in which a plain weave pattern 33' is circumferentially interspersed with a cross-weave pattern 35', which in this case is a leno weave. Parallel warp threads 32a' for forming the normal weave pattern 33' are alternated with warp threads 32b', 32c' which are crossed during formation of the leno weave pattern 35'. To weave the leno pattern, each of the crossed warp threads 32b',c' is held in the loom under generally equal tension. As in weaving the gauze pattern, each pick 30a' is shuttled through an opening formed between the cross points, as the pair of warp threads 32b',c' are twisted first one way and then the other way.

The relative pathways of the respective crossed warp threads 32b',c' in the leno weave pattern 35' is identical to the relative pathways of the respective crossed warp threads 32b,c in the gauze weave pattern. In the simple leno weave pattern, one of the crossed warp threads 32b' passes above every pick 30a' and the other crossed warp thread 32c' passes below every pick. The warp thread 32b' that passes above every pick 30a' passes below the other warp thread 32c' between adjacent picks. In the leno weave pattern 35', the crossed warp threads 32b',c' are of substantially equal length as represented in FIG. 4 by the similar sinuous configuration of crossed warp threads, as opposed to the gauze weave pattern where the doup thread 32c is illustrated in FIG. 3 as being much longer than the standard thread 32b. The relative positions of the two cross warp threads 32b' and 32c' are also preferably reversed in each successive cross-weave portion 35' as shown in FIG. 4.

A further weave pattern is the helical weave pattern 35", shown in FIG. 5, in which each of the warp threads 32b",c" alternatively passes above and below the picks 30a" and alternatively below and above each other between the picks. It may be noted that in the helical pattern, the crossing warp threads 32b", 32c" are truly intertwined with each other, whereas in the simple gauze or leno weaves, the warp threads are held in crossing relationship to each other by the picks 30a. A helical pattern is formed in a loom which twists the warp threads in the same direction between each passage of the weft shuttle. As in the above described embodiments, parallel warp threads 32a" are circumferentially alternated with the pairs of crossed warp threads 32b",c", resulting in the helical weave pattern 35" being circumferentially interspersed with a plain weave pattern 33".

A pure cross-weave throughout the graft would provide high resistance to unravelling; however, it is preferred that the longitudinally-extending normal weave pattern 33 be interspersed circumferentially between the cross-weave pattern 35. Alternating a normal weave pattern with a cross-weave pattern simplifies the loom on which the graft is woven by reducing the number of mechanisms required to twist the warp threads and by spacing these mechanisms apart. Because vascular grafts are woven tightly and from relatively low denier thread, generally at least one and preferably at least three parallel warp threads 32a are provided between each pair of crossed warp threads 32b,c for purposes of spacing the twisting mechanisms.

The normal weave pattern 32 also improves certain characteristics of the fabric and allows for better control of the tightness of the weave, thereby providing for more controlled and uniform porosity. The normal weave is also considered important for maintaining the shape of the graft, helping to assure that there are sufficient warp threads following a straight-line longitudinal path. This is particularly important when the cross-weave pattern 35 is a gauze weave because in a gauze weave, the space-filling doup threads are woven under considerably less tension than the standard threads and follow a more winding pathway.

The number of parallel threads 32a between successive pairs of crossed threads depends upon several factors, e.g., the denier of the thread and the diameter of the vascular prosthesis. To provide substantial resistance to unravelling, generally less than twenty and preferably less than twelve parallel warp threads 32a are interspersed between each pair of crossed warp threads. In most graft applications, it is found that between about three and about five parallel warp threads interspersed between each pair of crossed warp threads provides the best results, combining high resistance to unravelling and high suture hold with uniform porosity and good structure characteristics.

The normal weave pattern between the crossed warp threads is generally a 1/1 or plain weave because this provides the tightest weave with the lowest porosity; however, other weave patterns may be used, for example, to provide greater porosity if greater porosity is desired. Similarly, the cross-weave pattern could be such that two or more picks 30a are shuttled through each opening formed between adjacent cross points of the crossed warp threads; however, such patterns might provide somewhat less resistance to unravelling.

If a single parallel warp thread 32a is interspersed between each pair of crossed warp threads 32b,c, the picks 30a will pass above the parallel thread on one side of each pair of crossed warp threads and pass below the parallel thread on the other side of the crossed warp thread pair. Preferably, this is also the case when several parallel warp threads are interspersed between successive pairs of crossed warp threads.

It is preferred that the interspersed normal weave patterns 33 and cross-weave patterns 35 do not create a significant fabric surface pattern that might cause irritation within the body or collect dead tissue, and to this end the warp threads 32b,c which comprise the cross-weave pattern 35 may be individually thinner than the parallel warp threads 32a. Preferably however, the denier (weight per unit length) of the crossed warp threads 32b,c is between about 75% and about 100% of the denier of the parallel warp threads. For example, a graft may be woven from polyethylene glycol terephthalate, such as that sold under the tradename Dacron by Dupont, using 4 side-by-side strands of 34 filament, 70 denier Dacron for each parallel warp thread and 1 such strand for each crossed warp thread, together with 2 side-by-side strands of similar 70 denier Dacron for the continuous weft thread.

Threads useful for forming the prostheses according to the invention are synthetic fibers which are not degraded by the body. Multifilament Dacron or equivalent polyester fibers are the most preferred threads, as there has been substantial experience in using Dacron threads in vascular grafts, establishing that Dacron is biocompatible and long-lasting within the body. However, some other advantages are gained by employing multifilament polytetrafluorethylene threads, and they as well as many other synethetic yarns might be used.

The threads, which are initially spun as bundles of parallel filaments, are preferably texturized before the graft is woven in order to spread the filaments, whereupon when the threads are woven to form the graft, the spread filaments occupy the interstices formed by the crossing weft and warp threads. Texturizing is preferably accomplished by twisting the threads a controlled amount, heat-setting the threads in the twisted condition and then untwisting the heat-set threads. The texturized thread typically has about one-half twist per inch; usually this twist is dictated by the texturizing machine.

The graft 10, which is intitially woven in a flat tubular configuration as two overlaid, interconnected sheets, is appropriately shaped into its final configuration. The woven tube is placed on a cylindrical mandrel and then crimped, e.g., with a mold, to provide the circumferential pleats or corrugations 12 that help to maintain the graft in its open tubular configuration even as it is bent during surgery to accommodate to anatomical requirements. The open tubular configuration with the accordion-like corrugations is made permanent by heat-setting the shaped graft. Typically, the corrugated tube has a natural length that is about 40 percent of its precorrugated length, providing desired variability in the axial length of the graft.

After heat-setting, the graft is washed and dried several times, softening the fabric in the process. Then the graft is packaged and is sterilized within the package, e.g., by autoclaving or by exposing the packaged graft to a form of sterilizing radiation.

Illustrated in FIG. 6 is a shunt provided for an arteriosclerotic blood vessel 40 advantageously using a tubular graft 10 made in accordance with the present invention. Rather than remove a portion of the natural blood vessel 40 and replace the blood vessel portion with a graft, the graft 10 is used to form a bypass pathway, supplementing the passageway 41 that remains partially open in the arteriosclerotic blood vessel. Openings 42 are formed in the blood vessel wall at spaced-apart locations, and cut ends 44 of the graft 10 are sewn thereto with sutures 46. To avoid kinking the graft 10 while connecting it to the two openings 42 through the side of a generally straight-line blood vessel, the ends 44 of the graft are cut at an angle oblique to the axis of the graft. An ordinary woven graft with a simple weave pattern might not be suitable for forming this type of shunt because the continuous weft thread 30 would be severed multiple times by the diagonal cuts, and the individually severed weft segments would be prone to shred from the ends of the graft. In contrast, a graft woven according to the present invention can be used for such a shunt because the individually severed weft segments are each interlocked at multiple locations to the circumferentially interspersed cross-weave patterns 35.

When, for example, a 20 mm diameter tubular prosthesis is woven on a suitable loom, the warp pattern may utilize groups of three parallel warp threads 32a alternating with pairs of warp threads 32b,c crossed into a simple gauze pattern. The continuous weft thread 30 is shuttled through the three parallel warp threads in a normal 1/1 pattern while the gauze warp threads are twisted so that the picks 33a pass between every crossing of the warp threads. The weft thread 30 is formed by a multiplicity of yarns, for example 1 to 6 side-by-side strands of 70 denier Dacron. The parallel warp threads 32a could be formed of four side-by-side strands of 70 denier Dacron. The normal and doup warp threads 32b,c, which form the gauze pattern, could be formed of 40 to 70 denier Dacron. Each thread has a twist of about ½ twist per inch. The doup threads 32c are approximately two to five times as long as the normal warp threads 32b. Such a woven fabric 20 mm. tube may contain from about 400 to 600 parallel warp threads per inch and from about 40 to 60 pairs of crossed warp threads per circumferential inch and may also contain from about 45 to 80 picks (weft segments) per longitudinal inch. The measured porosity of the graft can range from as low as 20 to above 1000 ml/cm$^2$/min/120 mm Hg. In comparison, a graft knitted of similar threads having a comparable weight would have a porosity in the 2000–3000 ml/cm$^2$/min/120 mm Hg. range.

The woven graft is placed on a mandrel, crimped and heat-set, forming corrugations that reduce the length of the graft to about 40% of its woven length. Then the graft is washed and dried three times in a manner well known in the art, packaged and sterilized within the package in an autoclave.

The woven graft having a cross-weave pattern according to the invention is highly resistant to unravelling, even when placed under stress at the region of the sutures, and therefore has high suture hold whether it is in the form of a tubular vascular graft or a flat patch graft. Relative to a comparable knitted graft, this woven graft has greater strength, greater resistance to dilation, and more uniform porosity. Furthermore, less dead tissue build-up occurs on the interior surface of such a woven vascular graft than generally occurs on the interior surface of a high velour vascular graft.

While the invention has been described in terms of certain preferred embodiments, modifications obvious to one with ordinary skill in the art may be made without departing from the teachings of the present invention.

Various features of the invention are set forth in the following claims.

What is claimed is:

1. A vascular graft prosthesis comprising a tube formed of fabric insertable into the vascular system for the conveyance of blood therethrough, the fabric being a weave having a plurality of warp threads running the longitudinal direction and weft thread means running the circumferential direction, at least a portion of said warp threads at substantially regular intervals comprising pairs of warp threads that cross over each other with said weft thread means running between cross-over points of said crossed warp thread pairs, said weft thread means being restrained at each passage between said cross-over points against axial displacement, preventing unravelling of said weft thread means at ends of said prosthesis, the fabric being woven of a low porosity to promote retention of blood within said fabric prosthesis.

2. A vascular prosthesis according to claim 1 woven as a seamless tube, said weft thread means being a continuous weft thread helically winding through said warp threads.

3. A vascular prosthesis according to claim 1 wherein said normal weave pattern is a 1/1 weave.

4. A vascular prosthesis according to claim 1 wherein between about three and about twelve parallel warp threads are interspersed between successive pairs of crossed warp threads.

5. A vascular prosthesis according to claim 1 wherein between about three and about five parallel warp threads are interspersed between successive pairs of crossed warp threads.

6. A vascular prosthesis according to claim 1, the denier of the threads of each of said pairs being between about 75% to 100% of the denier of each parallel warp thread.

7. A vascular prosthesis according to claim 1 wherein said warp threads and said weft thread means are formed of material selected from the group consisting of polyethylene glycol terephthalate and polytetrafluoroethylene.

8. A vascular prosthesis according to claim 1 wherein said warp threads and said weft threads are multifilamentous.

9. A vascular prosthesis according to claim 8 wherein said multifilamentous threads are texturized.

10. A vascular prosthesis according to claim 1 wherein said crossed warp threads pairs and said weft thread means are woven into a gauze pattern.

11. A vascular prosthesis according to claim 1 wherein said crossed warp thread pairs and said weft thread means are woven into a leno pattern.

12. A vascular prosthesis according to claim 10 wherein said crossed warp thread pairs and said weft thread means are woven into a helical pattern.

13. A vascular prosthesis according to claim 1 wherein said prosthesis also includes a pair of bifurcated tube portions extending from one end of said tube, said tube portions being woven continuous of said tube.

14. A fabric adapted for use in a prosthesis for implanation into a living body, the fabric being a weave having a plurality of warp threads in one direction and weft thread means running in a generally perpendicular direction, pairs of warp threads that cross over each other with said weft threads means running between cross-over points of said crossed warp thread pairs and between about one and about twenty straight parallel warp threads interspersed between adjacent pairs of crossed warp threads with said weft thread means forming a normal weave pattern with said parallel warp threads, said weft thread means being restrained at each passage between said cross-over points from displacement in the running direction of said warp threads, preventing unravelling of said weft thread means at the ends of said warp threads.

15. A prosthesis according to claim 14 wherein between about three and about five parallel warp threads are interspersed between successive pairs of crossed warp threads.

16. A prosthesis according to claim 14 wherein said warp threads and said weft thread means are formed of material selected from the group consisting of polyethylene glycol terephthalate and polytetrafluoroethylene.

17. A prosthesis according to claim 14 wherein said crossed warp thread pairs and said weft thread means are woven into a gauze pattern.

18. A prosthesis according to claim 14 wherein said crossed warp thread pairs and said weft thread means are woven into a leno pattern.

19. A vascular graft prosthesis comprising a tube formed of fabric insertable into the vascular system for the conveyance of blood therethrough, the fabric being a weave having a plurality of warp threads running the longitudinal direction and weft thread means running the circumferential direction, pairs of warp threads that cross over each other with said weft thread means running between cross-over points of said crossed warp thread pairs, and between about one and about twenty straight parallel warp threads circumferentially interspersed between adjacent pairs of said crossed warp threads with said weft thread means forming a normal weave pattern with said parallel warp threads, said weft thread means being restrained at each passage between said cross-over points from axial displacement, preventing unravelling of said weft thread means at ends of said prosthesis, the fabric being woven of a low porosity to promote retention of blood with said fabric prosthesis.

20. A vascular prosthesis according to claim 19 wherein said warp threads and said weft thread means are formed of material selected from the group consisting of polyethylene glycol terephthalate and polytetrafluoroethylene.

21. A prosthesis according to claim 14 wherein said crossed warp thread pairs and said weft thread means are woven into a helical pattern.

* * * * *

UNITED STATES PATENT AND TRADEMARK OFFICE
CERTIFICATE OF CORRECTION

PATENT NO. : 4,530,113

DATED : July 23, 1985

INVENTOR(S) : Samuel A. Matterson

It is certified that error appears in the above-identified patent and that said Letters Patent is hereby corrected as shown below:

Column 3, line 51, change "of picks" to --or picks--.

Column 8, line 27, change "1" to --19--;

line 29, change "1" to --19--;

line 33, change "1" to --19--;

line 37, change "1" to --19--;

line 52, change "threads" to --thread--;

line 57, change "10" to --1--;

lines 64-65, correct the spelling of

--implantation--.

Signed and Sealed this

Twenty-first Day of January 1986

[SEAL]

Attest:

DONALD J. QUIGG

Attesting Officer       Commissioner of Patents and Trademarks